Figure 1:
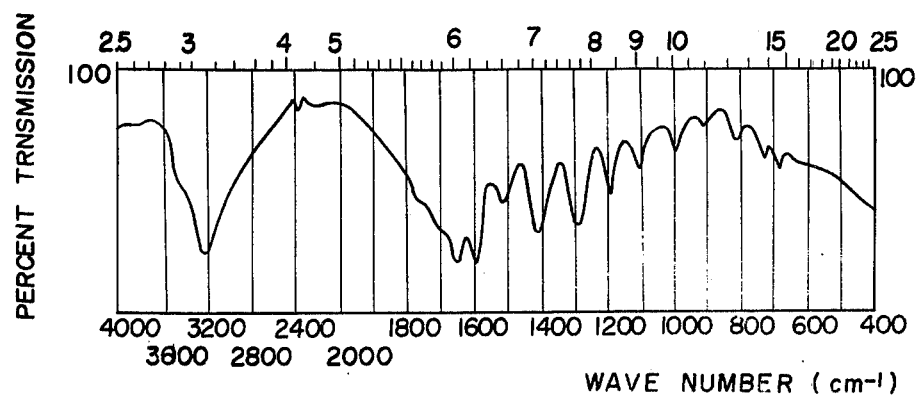

United States Patent [19]

Takayama et al.

[11] 4,025,525

[45] May 24, 1977

[54] ALLANTOIN COMPOUND WITH A METAL SALT OF 2-PYRROLIDONE-5-CARBOXYLIC ACID

[75] Inventors: Hirohide Takayama, Tokyo; Ippei Yoshimura, Mitaka, both of Japan

[73] Assignee: Kawaken Fine Chemicals Co., Ltd., Tokyo, Japan

[22] Filed: Sept. 16, 1975

[21] Appl. No.: 613,913

[30] Foreign Application Priority Data

Sept. 25, 1974 Japan .............................. 49-109509

[52] U.S. Cl. .............................. 260/299; 260/309.5; 424/245; 424/273

[51] Int. Cl.$^2$ .................. C07D 403/02; C07F 5/06

[58] Field of Search ......................... 260/299, 309.5

[56] References Cited

UNITED STATES PATENTS

| 3,107,252 | 10/1963 | Lubowe | 260/309.5 |
|---|---|---|---|
| 3,275,643 | 9/1966 | Lubowe | 260/299 |
| 3,290,324 | 12/1966 | Lubowe | 260/299 |
| 3,305,557 | 2/1967 | Lubowe | 260/299 |

FOREIGN PATENTS OR APPLICATIONS

| 1,940,477 | 2/1970 | Germany |
|---|---|---|
| 45-02750 | 1/1970 | Japan |
| 45-28796 | 9/1970 | Japan |
| 1,091,179 | 11/1967 | United Kingdom |

OTHER PUBLICATIONS

Lubowe Chemical Abstracts, vol. 63, 4096h, (1965).
Lubowe Chemical Abstracts, vol. 63, 17,802e, (1965).

*Primary Examiner*—Donald G. Daus
*Assistant Examiner*—D. G. Rivers
*Attorney, Agent, or Firm*—Woodhams, Blanchard and Flynn

[57] ABSTRACT

Allantoin compound with a metal salt of 2-pyrrolidone-5-carboxylic acid has a solubility which is from 2.5 to 4 times greater than that of pure allantoin. The compound has almost the same pharmacological effect as allantoin itself and is harmless, and therefore it can be used in medicines, cosmetics, creams, ointments, etc.

5 Claims, 3 Drawing Figures

ALLANTOIN COMPOUND WITH A METAL SALT OF 2-PYRROLIDONE-5-CARBOXYLIC ACID

BACKGROUND OF THE IVENTION

1. Field of the Invention

This invention relates to allantoin compound with a metal salt of 2-pyrrolidone-5-carboxlic acid.

SUMMARY OF THE INVENTION

It is an object of the present invention to provide a allantoin compound with a metal salt of 2-pyrrolidone-5-carboxylic acid.

It is another object of the present invention to provide a process for producing allantoin compound with a metal salt of 2-pyrrolidone-5-carboxylic acid.

It is still another object of the present invention to provide a compound having a greater solubility and moisturing effect than allantoin.

2. Detailed Description of the Invention

The compound obtained by combining allantoin with a salt of 2-pyrrolidone-5-carboxylic acid (hereinafter referred to as PCA) has the following formula:

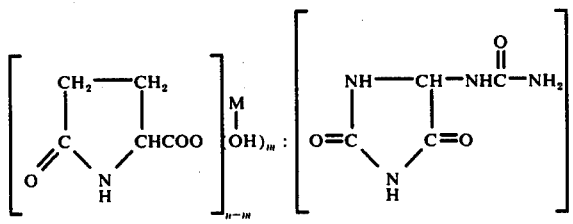

in which M represents lithium, potassium, sodium, calcium, magnesium, barium or aluminum; $n$ is an integer of one to three; M is zero; one or two and $(m+n)$ is the valence of M.

The solubility of allantoin in water is 0.03 mol/l. On the other hand, the solubility of allantoin derivatives of the above formula have the values shown in Table 1. As is apparent from Table 1, the solubility of allantoin·PCA sodium is 0.077 mol/l, that of allantoin·di(PCA)-calcium is 0.091 mol/l, and that of allantoin·tri(PCA)aluminum is 0.121 mol/l. Thus, the solubility of these derivatives is 2.5 to 4 times greater than that of pure allantoin and, in addition, the hygroscopicity thereof is far greater than that of allantoin.

Table 1

|  | Allantoin | Allantoin PCA sodium | Allantoin· di(PCA) calcium | Allantoin· tri(PCA) aluminum |
|---|---|---|---|---|
| Solubility(mol/l) | 0.033 | 0.077 | 0.091 | 0.121 |
| Quantity of water required to dissolve the quantity equivalent to 1g of allantoin at 25°C | 190 | 74 | 63 | 47 |
| Hygroscopicity | 1.8 | 26.6 | 28.0 | 28.0 |

In this table, hygroscopicity is defined as follows:

$$\text{Hygroscopicity} = \frac{\text{Weight of water absorbed in sample (g)}}{\text{Weight of sample (g)}} \times 100$$

It will be understood from Table 1 that, in the same quantity of water, the compound of the invention can be dissolved to supply much more allantoin in solution than the use of mere allantoin can do.

These novel compounds have melting points and decomposition points at fixed temperatures, respectively. In view of this fact and a comparison of infrared spectra of the compounds, allantoin combined with PCA salts, it can be concluded that the compounds are not mere mixtures of allantoin and PCA salts but rather are compounds in which allantoin and PCA salts are combined in a fixed ratio.

Figure 2:
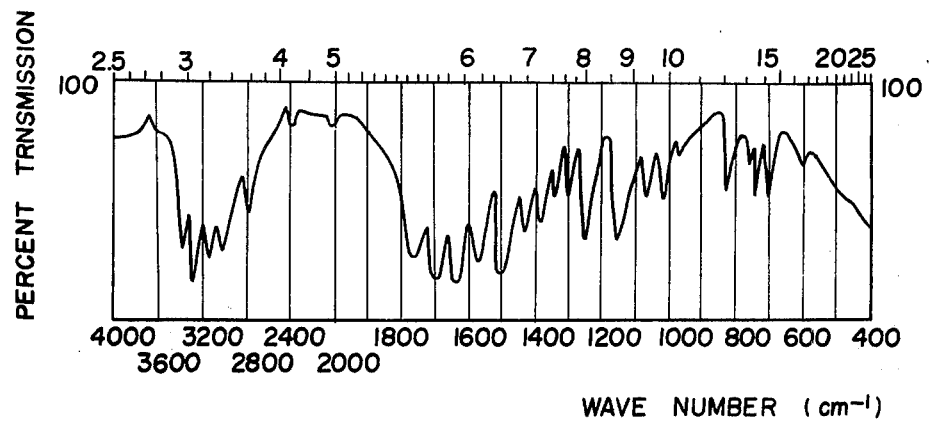
Figure 3:
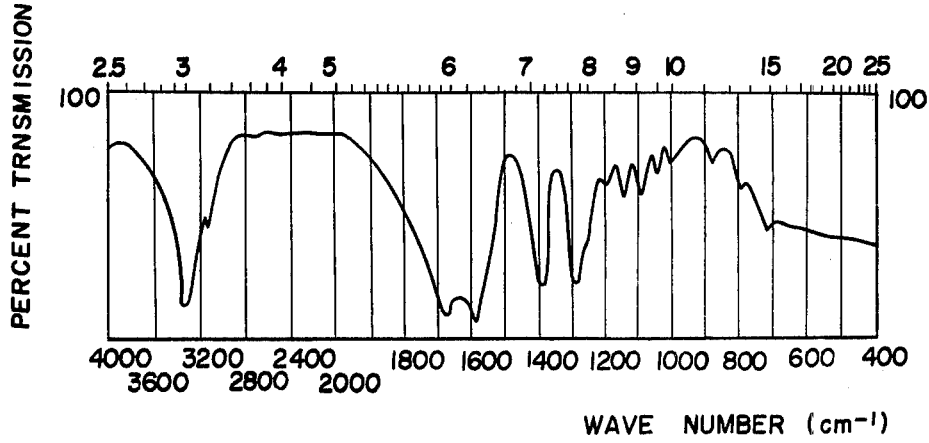

FIGS. 1, 2, and 3 show infrared absorption spectra, obtained by the KBr method, of allantoin PCA sodium, allantoin and PCA sodium, respectively.

Allantoin has a sedative action for injured skin, a cell propagation action, effects kerotolysis of skin, and has an action of eliminating necrotized tissue, etc. and therefore it has a wound healing effect and it is added to medicines, cosmetics, etc. However, it can not fully display its effect because its solubility in water, water-alcohol mixed solvents, etc. is small. On the other hand, the solubility of the compound of the invention in water and water-alcohol mixed solvents is greater than that of allantoin, and, in addition, the novel compound has almost the same pharmacological effect as allantoin itself and its action on the human skin is entirely harmless as will be described in detail later. Therefore, the novel compound can be used in medicines, cosmetics, creams, ointments, etc, thereby increasing the effect of allantoin.

PCA salts have a strong moisturizing effect and therefore are added to cosmetics, ointments, cleaning agents, etc. in order to maintain the moisture content of the products. However, PCA salts also have a weak vasodilator action which affects some persons strongly, and therefore their use in cosmetics is sometimes avoided.

On the other hand, the novel compound according to the present invention has a very mild vasodilator action which improves the skin permeability of components contained in cosmetics and the like.

Thus, the novel compound according to the present invention maintains the effects and characteristics of allantoin and PCA salt, and offsets the disadvantages thereof and, as a result, has excellent characteristics which each of allantoin and PCA salt or a mixture thereof do not have.

The process for producing the novel compound according to the present invention is carried out by heating allantoin and PCA salt, or allantoin salt and PCA, or allantoin, PCA and a metallic compound for transforming either allantoin or PCA into its salt, in an aqueous medium.

The aqueous medium employed includes a mixed solvent of water and hydrophilic organic solvent as well as water itself. The hydrophilic organic solvents include lower alcohols, lower keytones, dioxane, etc. PCA salts and allantoin salts include salts of alkali metals such as sodium and potassium, alkaline earth metals such as calcium and barium, and metallic salts of aluminum.

If the above-mentioned metal is divalent, two kinds of salts such as the di-PCA salt and hydroxy PCA salt are enumerated. If trivalent, three kinds of salts such as tri-PCA salt, hydroxy-di-PCA salt and di-hydroxy-PCA salt. are enumerated.

The metallic compound employed for transforming either allantoin or PCA into its salt includes sodium hydroxide, potassium hydroxide, sodium carbonate, sodium hydrogen carbonate, calcium hydroxide, barium hydroxide, aluminum hydroxide, Aluminium alcholate ($C_2 - C_4$), etc.

In view of the reaction velocity, the heating temperature is preferably 50° C to reflux temperature.

PREFERRED EMBODIMENTS OF THE INVENTION

EXAMPLE 1.

15.8 g of allantoin and 15.1 g of PCA sodium were added to 200 ml of water. The resulting solution was heated to 100° C while being stirred, and was kept at this temperature for one hour. Then, water was distilled from the reaction product under reduced pressure and the resultant crystals were placed in a desiccator to obtain 30.0 g of deliquescent white crystals. The decomposition point of the white crystals was 207° C, and the results of the elemental analysis thereof showed that the white crystals contained 35.03% of carbon, 4.04% of hydrogen, 32.01% of oxygen, 23.05% of nitrogen and 7.70% of sodium. These results are close to the calculated values for $C_9H_{12}O_6N_5Na$, which are 34.96% of carbon, 3.91% of hydrogen, 31.05% of oxygen, 22.65% of nitrogen, and 7.43% of sodium.

A comparison was made between the infrared absorption spectrum of this crystal shown in FIG. 1 and the infrared absorption spectra of allantoin and PCA sodium shown in FIGS. 2 and 3, respectively. Compared with FIG. 2 showing the spectrum of allantoin, in FIG. 1 the peaks of amide at 1425 cm$^{-1}$, 1355 cm$^{-1}$, and 1320 cm$^{-1}$ disappeared. Compared with FIG. 3 showing the spectrum of PCA sodium, in FIG. 1 the peak of carboxylate at 1675 cm$^{-1}$ were moved to 1655 cm$^{-1}$.

In view of the above results, it was found that the above-mentioned crystal was not a mere mixture of allantoin and PCA sodium but rather was a compound of a combination thereof.

EXAMPLE 2.

31.6 g of allantoin and 29.6 g of di(PCA) calcium were added to 200 ml of water. The mixture thus obtained was reacted at 80° C in a manner similar to that of Example 1 to obtain 60.0 g of deliquescent white crystals. The melting point of the white crystals was 112° to 115° C. The results of the elemental analysis thereof showed that the white crystal contained 37.60% of carbon, 4.04% of hydrogen, 32.00% of oxygen, 18.08% of nitrogen and 8.52% of calcium.

Assuming that the formula of this crystal is $C_{14}H_{18}O_9 N_6 Ca$, the above results were in good agreement with the calculated values therefor which showed 37.00% of carbon, 3.99% of hydrogen, 31.69% of oxygen, 18.49% of nitrogen and 8.83% of calcium. In view of these facts and the infrared absorption spectrum of this crystal, it was found that the above-mentioned crystal was a molecular compound as in the case of Example 1.

EXAMPLE 3

15.8g of allantoin and 25.6g of PCA were added to 300ml of water. The resulting solution was heated to 80° C while beining stirred and was added with 10g of calcuim hydroxide and further was kept for one hour at this temperature. Then unreacted calcium hydroxide was filtered off and the obtained filtrate was concentrated under reduced pressure to obtain crystals.

The resulting crystals were dried and the yield was 28.3g.

The melting point of the crystals was 112° to 115° C.

The results of the elemental analysis thereof showed that the white crystals contained 36.54% of carbon, 4.01% of hydrogen, 32.04% of oxygen, 18.4% of nitrogen, and 8.4% of calcium. Assuming that the formula of this crystal was $C_{14} H_{18} O_9 N_6 C_a$, the above results were in good agreement with the calculated values therefor.

EXAMPLE 4

1.58g of allantoin and 4.08g of tri(PCA) aluminium were added into 100 ml of water.

The resultant mixture was reacted at 95° C for 1.5 hours, according to the same procedure as that described in Example 1 to obtain 5.4g of deliquescent crystals.

The melting point of the crystals was 112°–118° C. The results of the elemental analysis thereof showed that the crystal is equivalant to a compound having the molecular formula of $C_{19} H_{24} O_{12} N_7 Al$.

Also, it was recognized from the infrared absorption spectra thereof that this crystal was a compound of allantoin combined with tri (PCA) aluminium.

EXAMPLE 5

1.58g of allantoin and 1.51g of PCA sodium was added into a mixture of 400g of methyl alcohol and 100 ml of water.

The resultant mixture was reacted for one hour at 70° C, according to the same procedure as that described in Example 1 to obtain 2.8g of white crystals.

The melting point of the crystals was 207° C (decomposition). The results of the elemental analysis thereof showed that this white crystals contained 34.80% of carbon, 3.85% of hydrogen, 31.55% of oxygen, 22.45% of nitrogen and 7.65% of sodium. The content of respective component of the crystals resembled closely that of $C_9 H_{12} O_6 N_5 N_a$.

EXAMPLE 6

15.8g of allantoin and 18.9g of PCAdihydroxyaluminium were added into 100 ml of water. The resultant mixture was heated at 90° C for one hour, according to the same procedure as that described in Example 1 to obtain 31g of deliquesent white crystals.

The melting point of the crystals was 215° C (decomposition). The result of the elemental analysis thereof showed that the crystals contained 33.10% of carbon, 3.65% of hydrogen, 37.98% of oxygen, 21.05% of nitrogen, and 8.18% of aluminum. These results resembled closely the calculated values for $C_9 H_{12} O_7 N_5$ all which are 32.83% of carbon, 3367% of hydrogen, 34.02% of oxygen, 21.28% of nitrogenand 8.2% of aluminium.

EXAMPLE 7

4 g of sodium hydroxide was added to 200 ml of water. Then, to the obtained solution 15.8 g of allantoin was added little by little with agitation to obtain a transparent solution of sodium allantoinate. This solution was heated to 80°C, and 12.8 g of PCA was added to this heated solution. Heating was continued for one hour to obtain a reaction product, from which water was distilled to obtain 32.1 g of white crystals.

The melting point of the crystals was 207° C (decomposition), and the results of the elemental analysis thereof showed that the crystals contained 34.79% of carbon, 4.01% of hydrogen, 31.65% of oxygen, 22.09% of nitrogen and 7.39% of sodium. These results were in good agreement with the calculated values for $C_6H_{12}O_6N_5Na$.

Then, in order to confirm the safety of the molecular compound allantoin-PCA sodium according to the present invention with respect to the human skin, a continuous open patch test and a closed patch test were conducted as follows:

1. Forty healthy males were selected as the subjects for the primary irritability of the open patch test. The left upper arm of each subject was marked with two frame-shaped marks each of a size of about 3×5 cm. A mixture of petrolatum (used as ointment base) and 10% of allantoin-PCA sodium were applied to one of the frames, and petrolatum was applied to the other of the frames for the purpose of comparison. These operations were conducted once a day for two weeks running. Observation of coated portions were conducted every day from the second day of test for three weeks running. As a result, no subjects were found who had abnormalities in the coated portions during the observation period.

Accordingly, it was confirmed that the compound under test caused no lesions to the skin by the open patch test conducted for two weeks.

2. Forty healthy males were selected as the subjects for the irritability of skin for the closed patch test. Petrolatum mixtures containing 0.5, 2, 8 and 32% of allantoin-PCA % of allantoin-PCA sodium were prepared, respectively. These mixtures were applied to the back of each subject using adhesive plasters (of standard size) for patch test produced by Torii Yakuhin Co., Ltd. For the purpose of comparison, a petrolatum-coated portion were added for test. The plasters were removed 48 hours after application to observe the existence and degree of efflorescence.

Observation was also made 72 hours after application (24 hours after removal of plasters) to examine the changes with the passage of time. Observation results were evaluated according to the evaluation standard shown in Table 2. The results of this evaluation were summed up and statistically processed to obtain the results shown in Table 3.

Table 2

| The Standard Score of Sympton | | |
|---|---|---|
| Symptom | Reading | Marks |
| No change | − | 0 |
|  | −~± | 1 |
| Erythema, partial | ± | 2 |
|  | ±~+ | 3 |
| Erythema, diffused | + | 4 |
|  | +~++ | 5 |
| Erythema with marked edema | ++ | 6 |

Table 3.

| Results of Closed Patch Test | | | | | |
|---|---|---|---|---|---|
| Time | Specimen | Concentration | Total of marks obtained | Average of marks obtained | Standard deviation |
| 48 hours after application | Comparison | Petrolatum | 8 | 0.200 | ± 0.56 |
|  |  | No coating | 3 | 0.075 | ± 0.26 |
|  | Allantoin-PCA sodium | 0.5 % | 4 | 0.100 | ± 0.37 |
|  |  | 2 | 3 | 0.075 | ± 0.26 |
|  |  | 8 | 12 | 0.300 | ± 0.84 |
|  |  | 32 | 18 | 0.450 | ± 0.74 |
| 72 hours after application | Comparison | Petrolatum | 1 | 0.025 | ± 0.16 |
|  |  | No coating | 0 | 0.000 | 0 |
|  | Allantoin-PCA sodium | 0.5 % | 0 | 0.000 | 0 |
|  |  | 2 | 0 | 0.000 | 0 |
|  |  | 8 | 5 | 0.125 | ± 0.33 |
|  |  | 32 | 8 | 0.200 | ± 0.46 |

In consideration of the above results, it could not be found that there was any significant difference between the primary irritability of skin in each concentration of allantoin-PCA sodium and the comparison.

What is claimed is:

1. A compound of the formula

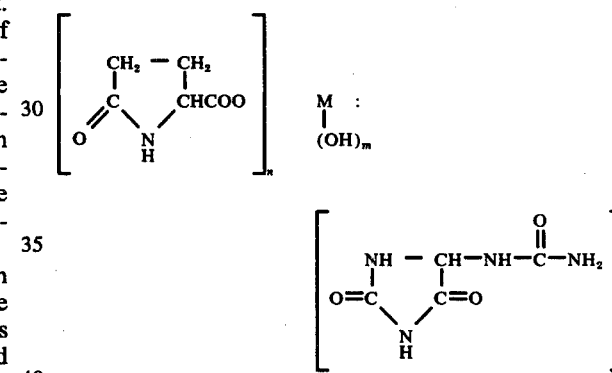

in which M is lithium, sodium, potassium, calcium, magnesium, barium or aluminum; n is an integer of one to three; m is zero, one or two; and ($m+n$) is the valence of M.

2. A compound according to claim 1, in which M is potassium.

3. A compound according to claim 1, in which M is sodium.

4. A compound according to claim 1, in which M is calcium.

5. A compound according to claim 1, in which M is aluminum.